United States Patent [19]
Adams et al.

[11] Patent Number: 5,641,658
[45] Date of Patent: Jun. 24, 1997

[54] METHOD FOR PERFORMING AMPLIFICATION OF NUCLEIC ACID WITH TWO PRIMERS BOUND TO A SINGLE SOLID SUPPORT

[75] Inventors: Christopher P. Adams, Winter Hill; Stephen Joseph Kron, Boston, both of Mass.

[73] Assignees: Mosaic Technologies, Inc., Winter Hill; Whitehead Institute for Biomedical Research, Cambridge, both of Mass.

[21] Appl. No.: 285,385

[22] Filed: Aug. 3, 1994

[51] Int. Cl.⁶ .................... C12P 19/34; C12Q 1/68
[52] U.S. Cl. ............................ 435/91.2; 435/6
[58] Field of Search ...................... 435/91.2, 6

[56] References Cited

U.S. PATENT DOCUMENTS 5,405,746  4/1995  Uhlen ............................ 435/6

FOREIGN PATENT DOCUMENTS

| | | |
|---|---|---|
| 374665 | 6/1990 | European Pat. Off. . |
| 487104 | 5/1992 | European Pat. Off. . |
| 2233654 | 1/1991 | United Kingdom . |
| WO9002205 | 3/1990 | WIPO . |
| WO9006042 | 6/1990 | WIPO . |
| WO9009455 | 8/1990 | WIPO . |
| 90/11369 | 10/1990 | WIPO . |
| WO9204469 | 3/1992 | WIPO . |
| WO9304199 | 3/1993 | WIPO . |
| WO9309250 | 5/1993 | WIPO . |
| WO94/24312 | 10/1994 | WIPO . |

OTHER PUBLICATIONS

Maskos et al, (1992), "Oligonucleotide hybridizations on glass supports: a novel linker for oligonucleotide synthesis and hybridization properties of oligonucleotides synthesised in situ", Nucleic Acids Res. 20(7):1679–1684.

Stamm et al, (1991), "Sanchored PCR: PCR with cDNA coupled to a solid phase", Nucleic Acids res. 19(6):1350.

Kaneoka et al, (1991), "Solid–phase direct DNA sequencing of allele specific polymerase chain reaction amplified HLA–DR genes", Biotechniques 10(1):30, 32, 34.

Saiki et al, "Genetic analysis of amplified DNA with immobilized sequence–specific oligonucleotide probes", Proc. Natl. Acad. Sci. USA 86:6230–6234.

*Primary Examiner*—George C. Elliott
*Assistant Examiner*—Jeffrey Fredman
*Attorney, Agent, or Firm*—Dann, Dorfman, Herrell and Skillman

[57] ABSTRACT

This invention features methods and apparatus for performing nucleic acid hybridization and amplification processes on a support. Such methods and apparatus are useful for synthesizing nucleic acid and detecting target nucleic acid for diagnostics and therapeutics.

13 Claims, 7 Drawing Sheets

METHOD FOR PERFORMING AMPLIFICATION OF NUCLEIC ACID WITH TWO PRIMERS BOUND TO A SINGLE SOLID SUPPORT

FIELD OF THE INVENTION

This invention features methods and apparatus for performing nucleic acid hybridization and amplification processes on a support. Such methods and apparatus are useful for synthesizing nucleic acid and detecting target nucleic acid for diagnostics and therapeutics.

BACKGROUND OF THE INVENTION

The following definitions are provided to facilitate an understanding of the present invention. The term "biological binding pair" as used in the present application refers to any pair of molecules which exhibit natural affinity or binding capacity. For the purposes of the present application, the term "ligand" will refer to one molecule of the biological binding pair and the term "antiligand" or "receptor" will refer to the opposite molecule of the biological binding pair. Two complementary strands of nucleic acid are biological binding pairs. One of the strands is designated the ligand and the other strand is designated the antiligand. However, biological binding pairs may also comprise antigens and antibodies, drugs and drug receptor sites and enzymes and enzyme substrates.

The term "probe" refers to a ligand of known qualities capable of selectively binding to a target antiligand. As applied to nucleic acids, the term "probe" refers to a strand of nucleic acid having a base sequence complementary to a target base sequence. Typically, the probe is associated with a label to identify a target base sequence to which the probe binds, or the probe is associated with a support to bind to and capture a target base sequence. The term "primer" is used to refer to nucleic acid having a base sequence complementary to a target base sequence, which upon nucleic acid hybridization is used to promote a reaction. These reactions usually involve enzymes called polymerases and transcriptases.

The term "label" refers to a molecular moiety capable of detection including, by way of example, without limitation, radioactive isotopes, enzymes, luminescent agents, dyes and detectable intercalating agents. The term "agent" is used in a broad sense, in reference to labels, and includes any molecular moiety which participates in reactions which lead to a detectable response. The term "cofactor" is used broadly to include any composition which participates in reactions with a label agent.

The term "support" refers to conventional supports such as beads, particles, dipsticks, fibers, filters, membranes and silane or silicate supports such as glass.

The term "amplify" is used in the broad sense to mean creating an amplification product which may include, by way of example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or transcriptases.

Genetic information is stored in living cells in threadlike molecules of deoxribonucleic acid (LNA). In vivo, the DNA molecule is a double helix, each strand of which is a chain of nucleotides. Each nucleotide is characterized by one of four bases: adenine (A), guanine (G), thymine (T), and cytosine (C). The bases are complementary in the sense that due to the orientation of functional groups certain base pairs attract and bond to each other through hydrogen bonding. Adenine in one stand of DNA pairs with thymine in an opposing complementary stand. Guanine in one strand of DNA pairs with cytosine in an opposing complementary strand. In ribonucleic acid (RNA), the thymine base is replaced by uracil (U) which pairs with adenine in an opposing complementary strand.

DNA consists of covalently linked chains of deoxribonucleotides and RNA consists of covalently linked chains of ribonucleotides. The genetic code of a living organism is carried upon DNA in the sequence of the base pairs. Proteins are made or expressed by living organisms in a process in which a DNA sequence is transcribed to a RNA sequence and the RNA sequence translated into proteins.

Each nucleic acid is linked by a phosphodiester bridge between the five prime hydroxyl group of the sugar of one nucleotide and the three prime hydroxyl group of the sugar of an adjacent nucleotide. Each linear strand of naturally occurring DNA or RNA has one terminal end having a free five prime hydroxyl group and another terminal end having a three prime hydroxyl group. The terminal ends of polynucleotides are often referred to as being five prime (5') termini or three prime (3') termini in reference to the respective free hydroxyl group. Complementary strands of DNA and RNA form antiparallel complexes in which the 3' terminal end of one strand is oriented to the 5' terminal end of the opposing strand.

Nucleic acid hybridization assays detect the tendency of pairs of nucleic acid strands to pair with greatest stability if they contain regions of complementary sequence. Each pair of complementary nucleotides, between two strands, increases the stability of pairing between a biological binding pair formed between the two nucleic acids. DNA segments isolated from a growing organism are generally duplex DNA, a pair of perfectly complementary strands whose pairing is very stable. The term "hybridize" refers to imposing conditions which promote such pairing. The term "denature" refers to imposing conditions which discourage such pairing. These conditions are imposed by adjusting ionic strength, pH or temperature.

Polymerases and transcriptases are enzymes which, in the presence of appropriate reaction conditions, produce complementary copy of a strand of DNA or RNA. The strand that is copied is called the template DNA or RNA.

A polymerase chain reaction, PCR, uses a pair of nucleic acid primers to synthesize copies of target nucleic acid. One primer hybridizes to a target sequence on a first strand, and a second primer hybridizes to a second target sequence on the second strand. This permits the amplification product directed by one of the pair of primers to serve as a template for synthesis directed by the second member of the pair of primers. PCR is carried out using a solution containing both members of the pair of primers and a polymerase capable of withstanding conditions required to denature paired strands of DNA.

The identification of unique DNA or RNA sequence or specific genes within the total DNA or RNA extracted from tissue or culture samples may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle cell anemia, tissue compatibility, cancer and precancerous states, or bacterial or vital infections. The identification of unique DNA or RNA sequences or specific genes within the total DNA or RNA extracted from bacterial cultures or tissue containing bacteria may indicate the presence of antibiotic resistance, toxins, viruses, or plasmids, or provide identification between types of bacteria.

Thus, nucleic acid hybridization assays have great potential in the diagnosis and detection of disease. Further potential exists in agricultural and food processing where nucleic acid hybridization assays may be used to detect plant pathogenesis or toxin-producing bacteria.

Much research is presently directed to identifying the nucleic acid sequences which define organisms. An initial step in the process is the identification of regions within the nucleic acid, a process known mapping. These regions may be subjected to further sequencing. Both the mapping process and the sequencing process are slow and tedious.

SUMMARY OF THE INVENTION

The present invention features methods, articles of manufacture and devices for forming an amplification product in the presence of a first nucleic acid having a target sequence. The methods, articles of manufacture and devices feature the amplification of a first nucleic acid without the use of solution base primer pairs. The method, articles of manufacture and instruments allow the performance of multiple simultaneous amplification reactions for rapid analysis of nucleic acids. The amplification reactions do not require the presence of an external reaction chamber, or the presence or use of gels for the analysis of the amplification product.

One embodiment of the present invention features a method for forming an amplification product in the presence of a first nucleic acid having a first target sequence. The method comprises the steps of forming an immersion product comprising a sample potentially containing the first nucleic acid, and a support. The support has a second nucleic acid having a sequence complementary to the target sequence. The second nucleic acid is covalently linked to the support. The method further comprises the step of forming a hybridization product comprising the first nucleic acid and the second nucleic acid, in the event the first nucleic acid is present in the sample. The hybridization product is formed by imposing hybridization conditions on the immersion product. The method further comprises the step of forming a first amplification product comprising a nucleic acid complementary to the first nucleic acid covalently extending from said second nucleic acid.

Preferably, the first nucleic acid comprises a second target sequence and the support comprises a third nucleic acid homologous to the second target sequence. Preferably, the method further comprises the step of releasing the first nucleic acid from the second nucleic acid by imposing the denaturation conditions on the immersion product. Release of the first nucleic acid allows the first nucleic acid to participate in further hybridization reactions.

Preferably, the release of the first nucleic acid also allows the amplification product to participate in further hybridization reactions to form a second hybridization product. Preferably, the method further comprises imposition of a second step of hybridization conditions to form at least one second hybridization product. The second hybridization product comprises the first amplification product and a third nucleic acid or the first nucleic acid and a further second nucleic acid. Preferably, upon imposition of second hybridization conditions on the immersion product, the third nucleic acid forms a second hybridization with the first amplification product.

The formation of the second hybridization product allows the additional step of forming a second amplification product comprising nucleic acid complementary to the first amplification product covalently extending from the third nucleic acid. Thus, the first nucleic acid and the first and second amplification products, are capable of participating in a plurality of hybridization and amplification processes, limited only by the initial presence of the first nucleic acid and second and third nucleic acids initially present. Preferably, a plurality of second and third nucleic acids are covalently linked to the support to provide a plurality of first and second amplification products.

Preferably, the second nucleic acid and the third nucleic acid have positions on the support, which are spaced a distance less than the length of the first nucleic acid to allow an amplification product to form between the second and third nucleic acids. Preferably, a plurality of second and third nucleic acids have positions on the support, which are spaced a distance less than the length of the first nucleic acid, to form a plurality of first and second amplification products.

Preferably, the method further comprises the step of monitoring the support for the presence of one or more amplification products which one or more amplification products are indicative of the presence of one or more target sequence and which absence is indicative of the absence of a target sequence. The formation of a plurality of first and second amplification products allows the detection of extremely small numbers of first nucleic acid having target sequence.

Preferably, the support is epoxy silane derivatized silica. Supports may be filters, fibers, membranes, beads, particles, dipsticks, sheets, rods and the like. Preferably, the support has a composition of plastic, such as nylon or latex for beads, particles, dipsticks and the like; or glass, in the form of glass fiber, glass sheets, beads, rods, dipsticks; or metal, in the form of magnetic particles and the like. A preferred support comprises a sheet which has surfaces with alignment features to allow the precise positioning of the second nucleic acid and third nucleic acids, to define areas of the support directed to a first pair of target sequences and other areas directed to a second pair of target sequences. These areas are preferably arranged in a grid type pattern of pixels.

Preferably, the second nucleic acid is covalently bonded to a hexaethylene glycol functional group which functional group is covalently bonded to the support. However, other functional groups can be used to covalently bond DNA with a support. Preferably, the second nucleic acid is covalently bonded to the hexaethylene glycol functional group to a 5' amino group. The hexaethylene glycol functional group positions the second nucleic acid away from the support to allow the second nucleic acid to interact with the first nucleic acid and enzymes used to form the amplification product.

Preferably, the first nucleic acid has a size of approximately 1 to 10 kb. Larger nucleic acids can be readily digested by enzymes or mechanically fragmented. Preferably, the second and third nucleic acid have a density or concentration on the support to allow spacing between such second and third nucleic acid less than the size of the first nucleic acid. Thus, the size of the first nucleic acid cooperates with the density concentration or spacing of second and third nucleic acids to allow amplification products to form there between.

As used herein, the term "immersion product" refers to a support that is covered with a sample and other reagents about the nucleic acids covalently bonded to its surface. By way of example, waking an immersion product may comprise placing a dipstick into a solution or placing beads in a solution, or wetting a slide or glass surface with a solution.

The term "hybridization product" refers to the product of a hybridization reaction. The term "amplification product" refers to a molecule or part of a molecule which has been made or extended by virtue of another molecule being present. Preferably, the amplification product is formed by imposing amplification conditions on the immersion product. Amplification conditions comprise applying a thermal stable polymerase nucleotides and other necessary reagents for a polymerase reaction to the hybridization product under conditions of temperature, ionic strength, and pH to support a polymerase reaction. As used herein, the term "applying" means contacting or placing in proximity of an object in a manner such that the subject may act upon the object in the intended manner.

Preferably, the amplification product incorporates a label capable of detection. Preferred labels include radioisotopes, and chemiluminescent, luminescent and fluorescent agents and cofactors. However, where the amplification product participates in hybridization reactions to form a further hybridization product, such product can be detected with intercalating agents. In the alternative, the amplification product can be detected by a fourth nucleic acid probe which probe is complementary or homologous to a third target sequence derived from the first nucleic acid and present on one or more of the amplification products. The fourth nucleic acid probe detects the correct nucleic acid sequence of the amplification product to reduce false positives.

Embodiments of the present method can be used to quantitate the amount of first nucleic acids having a target sequence. The number of cycles and the amount of signals generated by the amplification product relate to the amount of first nucleic acid having a target sequence initially present.

One embodiment of the present method features a support with many sets of second and third nucleic acids, with each set directed to a different first nucleic acid. Preferably, each set of second and third nucleic acids are positioned in discrete areas of the support. Each support may comprise a plurality of sets to a plurality of first nucleic acids and targets. Preferably, at least one set has a second and third nucleic acid having a nonsense sequence, which nonsense sequence is not intended under hybridization and amplification conditions to generate an amplification product as a negative control. Preferably, at least one set has a second and third nucleic acid having a sequence which is universally present in almost all samples, or is directed to a nucleic acid sequence present in the sample as a positive control.

Embodiments of the present method are also useful for mapping large nucleic acids. One embodiment of the present invention features sets of second and third nucleic acids. Each set is directed to a first nucleic acid which first nucleic acid is part of a large nucleic acid. The sets of second and third nucleic acids generate sets of first and second amplification products. The sets of first and second amplification products span overlapping sequences of the large nucleic acid. As used herein, "overlapping" refers to two nucleic acids having at least one identical nucleotide sequence directed to an area of nucleic acid from which they were derived or to which they are intended to hybridize. These overlapping sequences can be correlated to produce a map of the large nucleic acid. The present invention can be used to replace the use of sequence tag sites by using an array of amplification products.

One embodiment of the present invention features a method which is capable of forming a precipitate or agglutination product in the presence of a first nucleic acid having a target sequence. This method features a first support having a second nucleic acid and a second support having a third nucleic acid. The method comprises forming an immersion product of the first and second support with a sample potentially containing the first nucleic acid. Next, hybridization conditions are imposed on the immersion product to form a first hybridization product comprising the first nucleic acid and the second nucleic acid. Next, amplification conditions are imposed on the hybridization product to form a first amplification product. The third nucleic acid has a sequence identical to a second target sequence. That is, the third nucleic acid is complementary to at least a section of the first amplification product. The method further comprises forming a second hybridization product comprising the third nucleic acid and the first amplification product extending from the first support. This second hybridization product can promote an agglutination or precipitation of the immersion product.

Preferably, this hybridization product is further stabilized by forming a second amplification product comprising a nucleic acid extending from the third nucleic acid complementary to the first amplification product.

Preferably, the immersion product comprises a suspension of supports. Each support having a plurality of second and third nucleic acids which upon cycling through hybridization, denaturation and amplification conditions form an agglutination product.

The present method is ideally suited for applications utilizing carboxylated latex particles, plastic or glass beads which can precipitate from solutions upon the formation of a second hybridization product or a second amplification product.

A further embodiment of the present invention features an article of manufacture for forming an amplification product in the presence of a first nucleic acid having a target sequence. The article of manufacture comprises a support having a second nucleic acid having a nucleotide sequence complementary to the target sequence, which second nucleic acid is covalently bound to the support. The support is capable of forming an immersion product with a sample potentially containing the first nucleic acids, undergoing hybridization conditions and undergoing amplification conditions to form a first hybridization product and a first amplification product in the presence of the first nucleic acid. The first amplification product extends from the second nucleic acid and is complementary to the first nucleic acid.

Preferably, the article of manufacture further comprises a third nucleic acid in which the third nucleic acid is complementary to the first amplification product. The third nucleic acid is capable of forming a second hybridization product with a target sequence of the first amplification upon imposition of hybridization conditions. That is, the third nucleic acid is homologous to a second target sequence of the first nucleic acid. Preferably, the third nucleic acid is capable of priming a reaction to form a second amplification product.

Preferably, the second and third nucleic acid have a spaced relationship. The positions are separated by a distance less than the length of the first target sequence and the second target sequence of the first nucleic acid. In the alternative, the second and third nucleotides are randomly immobilized in a concentration or density on the support such that first and second nucleic acids have a spaced relationship.

Preferably, each set occupies a defined region of the support to form a pixel-like area. The amplification product occurs in the defined region and is termed the test site or test pixel.

Preferably, in order to effect mapping of a first nucleic acid, the support has a plurality of sets of second and third nucleic acids. Each set corresponds to a first nucleic acid which first nucleic acid is part of a large nucleic acid. The first nucleic acid for each set preferably has overlapping sequences to allow mapping of the first nucleic acid by matching the overlapping area.

Embodiments of the present invention are well suited for automation. A further embodiment of the present invention features an instrument for forming an amplification product in the presence of a first nucleic acid having a target sequence. The instrument comprises means for receiving a support having a second nucleic acid having a nucleotide sequence complementary to the target sequence. The second nucleic acid is covalently bound to the support. The instrument further comprises means for forming an immersion product comprising the support and the sample. The instrument further comprises means for imposing hybridization conditions on the immersion product for forming a hybridization product in the presence of the first nucleic acid. The instrument further comprises means for imposing amplification conditions on the hybridization product, if formed, to form an amplification product. The formation of the amplification product can be related to the presence of the first nucleic acid and the target sequence.

Means for forming an immersion product may comprise apparatus for depositing a sample on a support containing the second nucleic acid or means for placing the solid support within a containment vessel containing the sample.

Means for imposing hybridization conditions comprises devices such as dispensing orifices, pipettes and the like for placing suitable buffers with the immersion product and temperature controls to effect hybridization of nucleic acid, Means for imposing amplification conditions comprises devices such as dispensing orifices, pipettes and the like for placing enzymes and reagents for extending nucleic acid or duplicating nucleic acid. Typical reagents include polymerases, nucleotides, buffers and the like. The conditions for imposing hybridization conditions and amplification conditions are well known to individuals skilled in the art.

Thus, the present invention features methods, devices and articles of manufacture for the detection of nucleic acid having a particular target sequence without using solution based primer sets. The present invention facilitates the performance of simultaneous target amplification reactions, greatly shortening the time to generate data necessary to map nucleic acids. The absence of an external reaction chamber and a gel base system for the analysis of amplified products greatly facilitates the analysis of the assay results.

These and other features will become apparent from the drawings and the detailed description which follow which, by way of example, without limitation, describe preferred embodiments of the present invention.

DETAILED DESCRIPTION OF THE INVENTION

This invention features methods and apparatus for performing nucleic acid hybridization and amplification processes on a support. The practice of the present invention will employ, unless otherwise indicated, conventional techniques of chemistry, molecular biology, microbiology, recombinant DNA and immunology, which are within the skill of the art. Such techniques are explained fully in the literature. See: for example, e.g., Maniatis, Fritch and Sambrook, Molecular Cloning: A Laboratory Manual (1982); DNA Cloning, Volumes 1 and 2 (D.N. Glover Ed. 1985); Oligonucleotide Synthesis (M.J. Gait ed, 1984); Nucleic Acid Hybridization (B.D. Hames & S. J. Higgins eds. 1984); the series, Methods in Enzymology (Academic Press, Inc.), particularly Vol. 154 and Vol. 155 (Wu and Grossman, eds.).

Figure 1A:
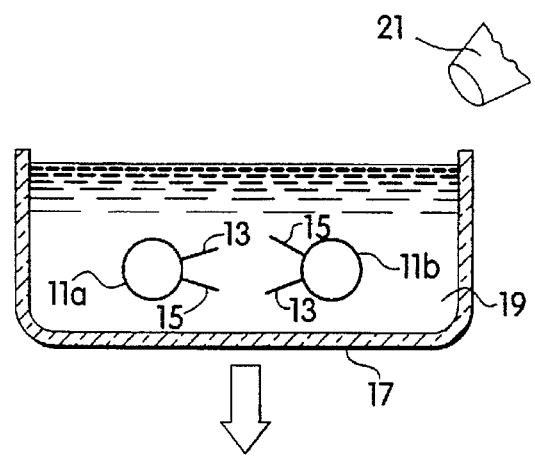
FIGS. 1A through 1M depict schematically a method, article of manufacture and instrument for making amplification products.
Figure 1B:
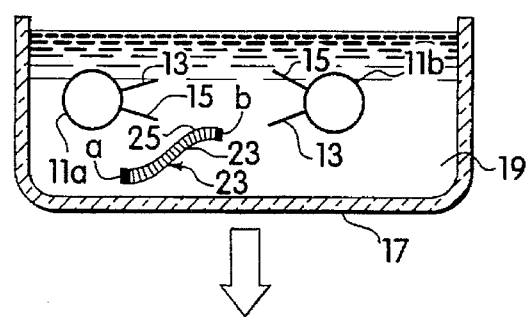
Figure 1C:
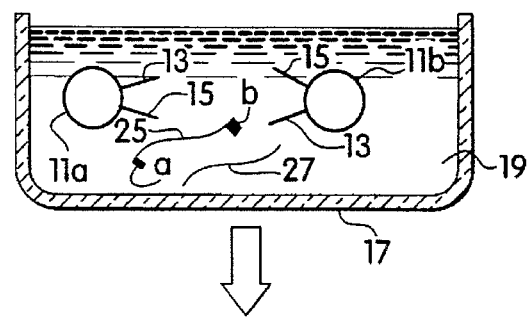
Figure 1D:
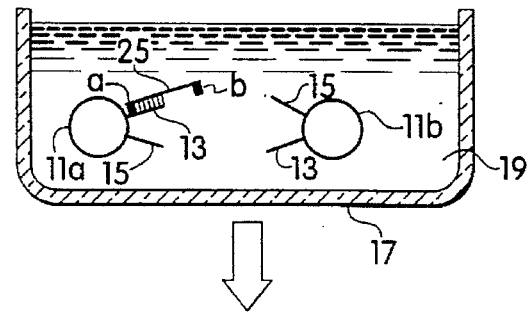
Figure 1E:
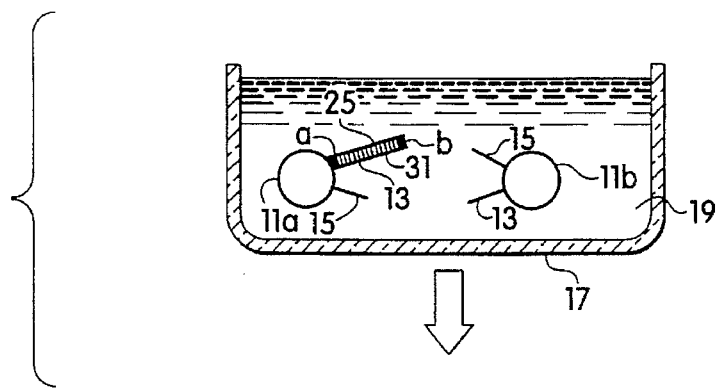
Figure 1F:
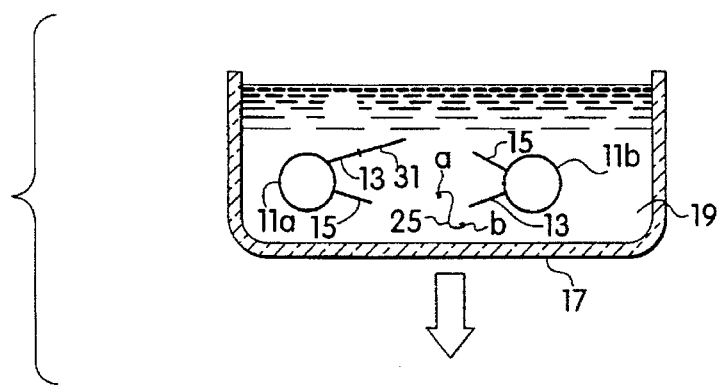
Figure 1G:
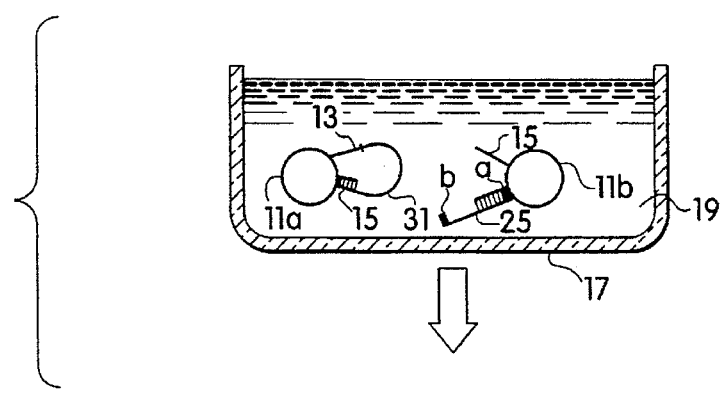
Figure 1H:
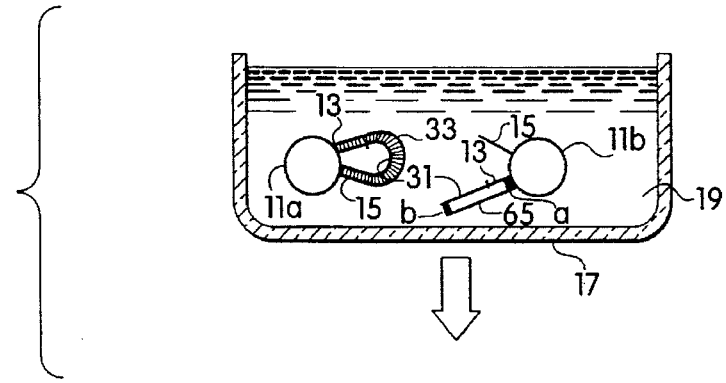
Figure 1I:
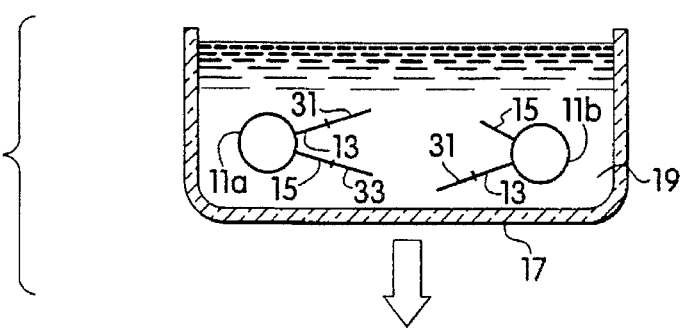
Figure 1J:
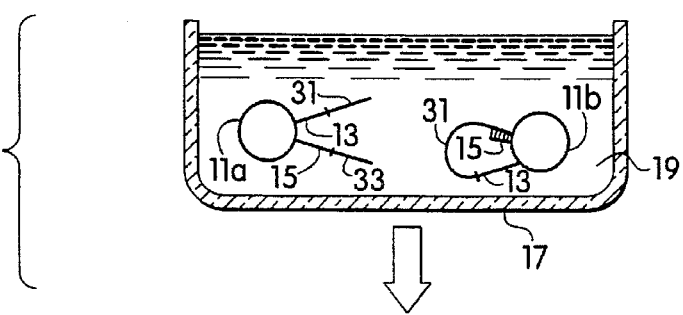
Figure 1K:
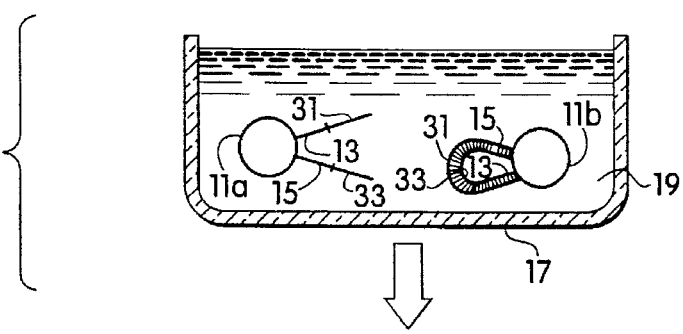
Figure 1L:
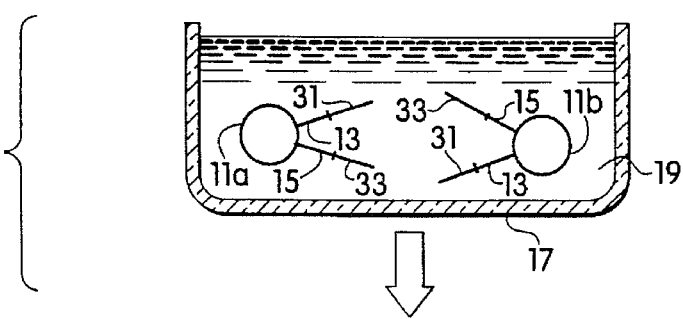
Figure 1M:
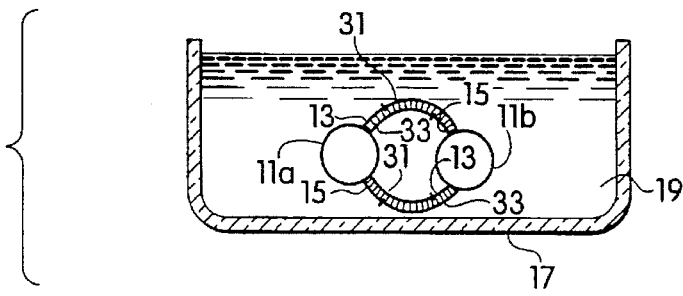

Turning now to FIGS. 1A and 1M, an article of manufacture, a plurality of carboxylated latex beads, generally designated by the numeral 11a and 11b, for making an amplification product is depicted. The presence of an amplification product will be used to indicate the presence of two target sequences of a first nucleic acid. Latex beads 11a and 11b have at least one second nucleic acid, and preferably, a plurality of second nucleic acids which will act as primers in an amplification reaction. The second nucleic acid is affixed covalently through a 5' linkage and the carboxylated functional group of the latex bead. As illustrated, each latex bead 11a and 11b has a second nucleic acid 13 and a third nucleic acid 15 for purposes of simplicity, with the understanding that many more second and third nucleic acids 13 and 15 may be present. The representations of the latex beads 11a and 11b and second and third nucleic acids 13 and 15 are for illustrative purposes and are not drawn to scale.

The methods of the present invention can be performed manually or in an automated instrument. In an instrument format FIGS. 1A–1M represent an instrument. Each FIG. 1A to 1M represents a work station with a double arrow representing conveying means. Conveying means may comprise rotatable turntables, conveying belts and the like.

In FIG. 1A, latex beads 11a and 11b are depicted as being suspended in a aqueous solution 19 contained within a vessel 17. Solution 19 and/or beads 11a and 11b are dispensed into vessel 17 by a dispensing orifice 21 or may be prepackaged in vessel 17.

FIG. 1B illustrates the addition of a first nucleic acid 23 derived from a sample, to vessel 17. First nucleic acid 23 may be placed in vessel 17 prior to beads 11a and 11b or after as illustrated. First nucleic acid 23 may be placed in vessel 17 by means of an orifice such as orifice 21 depicted in FIG. 1A. First nucleic acid 23 is double stranded DNA, comprising a first strand 25 and a second strand 27. Each strand has two target sequences a and b. Second nucleic acid 13 is complementary to target sequence a of strand 25 and homologous to sequence a of strand 27. Third nucleic acid 15 is homologous to target sequence b of strand 25 and complementary to sequence b of strand 25. First nucleic acid 23 and latex beads 11a and 11b form a immersion product.

FIG. 1C depicts the immersion product, latex beads 11a and 11b and first nucleic acid undergoing denaturation conditions. Denaturation conditions are imposed at a work station by suitable means such as controlling temperature, and/or ionic strength, and/or the pH of solution 19 contained in vessel 17.

The immersion product, comprising the first nucleic acid and the latex beads 11a and b, is next subjected to hybridization condition as represented in FIG. 1D. Hybridization conditions are preferably performed at a work station by adjusting one or more factors influencing hybridization, including temperature, and/or ionic strength and pH.

FIG. 1D depicts a hybridization product comprising first nucleic acid strand 25 and second nucleic acid 13 of latex bead 11a. First nucleic acid strand 27 may also have target areas [not shown] which interact with further primers [not shown]. For purposes of simplicity and clarity, this discussion will focus on strand 25 and target sequence a and b.

The hybridization product, comprising first nucleic acid stand 25 and second nucleic acid 13 of latex bead 11a, is next subjected to amplification conditions, as represented in FIG. 1E. Amplification conditions are preferably imposed at a work station by adding suitable reagents for amplification, including a thermal stable polymerase, nucleotides and other necessary reagents, buffers and the like. Thus, a work station as represented by FIG. 1e will receive vessel 17 and add suitable reagents through orifices such as orifice 21 depicted in FIG. 1a. FIG. 1e depicts a first amplification product 31 covalently extended from first nucleic acid 13. This amplification product is complementary to first nucleic acid strand 25. Thus amplification product 31 has a target sequence b which is complementary to third nucleic acid 15 of latex beads 11a or 11b.

The first amplification product is next subjected to denaturation conditions at a further work station, as illustrated in FIG. 1F. Upon imposition of denaturation conditions, a denaturation product is formed comprising first nucleic acid strands 25 and 27; second and third nucleic acids 13 and 15 of latex beads 11a and 11b; and a first amplification product 31 as illustrated in FIG. 1F. Denaturation conditions comprises elevated temperatures, higher salt concentrations and/or lower pH. The work station has means for imposing denaturation conditions such as an orifice 21 depicted in FIG. 1a for adding reagents or heating elements [not shown].

The denaturation product is next subjected to hybridization conditions at a further work station as illustrated in FIG. 1G. Upon imposition of hybridization conditions, a hybridization product is formed. In one alternative, the hybridization product comprises the first amplification product 31 and third nucleic acid 15 of latex bead 11b; and the first nucleic acid strand 25 and second nucleic acid 13 of latex bead 11b. In the alternative, as illustrated in FIG. 1G, a hybridization product forms comprising the first amplification product 31 and third nucleic acid 15 of latex bead 11a; and the first nucleic acid strand 25 and second nucleic acid 13 of latex bead 11b.

Upon imposition of amplification conditions, as illustrated in FIG. 1H, a second amplification product 33 is formed. The second amplification product extends from third nucleic acid 15 of latex bead 11a. In the alternative, a second amplification product 33 is formed extending from third nucleic acid 15 of latex bead 11b. A further first amplification product 31 is formed from first nucleic acid 13 of latex bead 11b.

Imposition of further cycles of denaturation, hybridization, amplification and denaturation as depicted in FIG. 1I–FIG. 1L, form additional first and second amplification products 31 and 33 extending from each second and third nucleic acid 13 and 15 of each latex bead 11a and b. Preferably, the cycles of denaturation, hybridization, amplification and denaturation are performed at work stations. These cycles can be repeated as many times as desired until the second and third nucleic acids 13 and 15 are exhausted.

First and second amplification products 31 and 33 hybridize to each other and allow hybridization between adjacent latex particles 11a and 11b as depicted in FIG. 1M. Preferably, hybridization conditions are imposed at a work station of an instrument. The hybridization of first and second amplification products 31 and 33 of adjacent latex beads 11a and 11b disrupts the suspension and the beads 11a and 11b precipitate or agglutinate into a detectable mass. Preferably, this detectable mass is detected by monitoring equipment [not shown]. The formation of the detectable mass is indicative of the presence of the first nucleic acid and, in particular, target sequences a and b of strand 25.

Turning now to FIGS. 2A through 2J, and in particular, an article of manufacture, generally designated by the numeral 111, for making an amplification product in the presence of a first nucleic acid, is depicted. The article comprises an epoxy silane derivatized support 113 which support has a planar upper surface 117 with two areas 121 and 123. Areas 121 and 123 each contain a probe set comprising a second and a third nucleic acid. The second and third nucleic acids of area designated 121 are designated 125 and 127 respectively. The second and third nucleic acids of area 123 are designated 125' and 127' prime respectively. The representations of the nucleic acids and areas 121 and 123 are for illustrative purposes only and are not drawn to scale. The areas are preferably pixel sized, as the term pixel is used with respect to a television screen. These areas are preferably areas of 10 $\mu^2$ to 1 $mm^2$.

The support 113 may take many different forms, such as sheets of glass, beads or dipsticks. Individuals skilled in the art can readily modify the shape and size of the support in order to fit individual needs. The entire support 113 may be any convenient size; however, preferably it is shaped to present a planar upper surface 117 of approximately 1 $cm^2$.

Figure 2A:
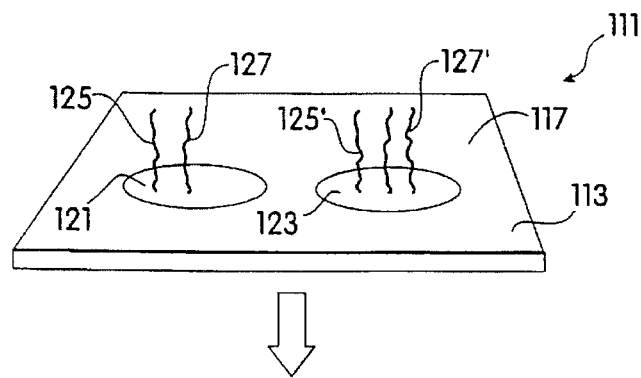
FIGS. 2A though 2L depict schematically a method, article of manufacture and instrument for making amplification products in accordance with the present invention.
Figure 2B:
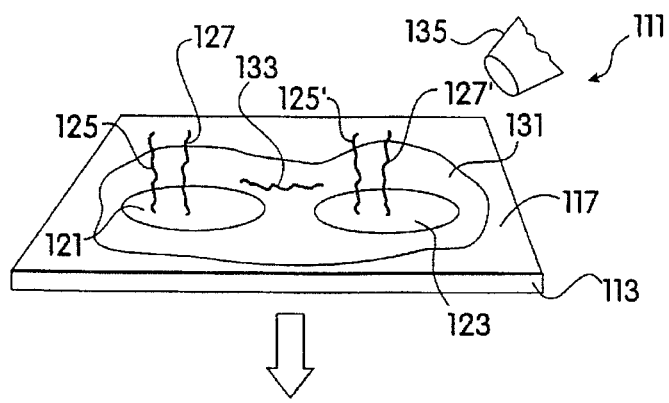

Turning now to FIG. 2B, a sample, generally designated by the numeral 131, is deposited on the support 113 forming an immersion product. Individuals skilled in the art will readily recognize that the support 113 can be totally immersed in a solution or a solution deposited upon the surface of the support in order to apply a sample to the nucleic acid of areas 121 and 123. Sample 131 has a first nucleic acid 133 having target sequences complementary to the second nucleic acid of region 121 and 123. As depicted, means for applying the sample 131 to support 113 comprise a sample dispensing orifice 135.

The methods of the present invention can be performed manually or in an automated instrument. In an instrument format, each Figure represents work stations, with a double arrow representing conveying means. Conveying means may comprise rotatable turntables, conveying belts and the like.

In another format the methods of the present invention can be performed in a self contained reaction cartridge. Typically, the cartridge contains all of the necessary reagents needed to perform the assay. The cartridge will have a port for introduction of the sample and separate isolated chambers for buffers, enzymes, and detection agents, e.g., dyes or labeled oligonucleotides. The use of microfabrication techniques to manufacture the cartridge leads to increased reaction speeds and reduced reagent concentrations. At programmed intervals, reagents are released from the reagent chambers and delivered to the central reaction site, containing the first target nucleotide and the immobilized second and third oligonucleotides.

Figure 2C:
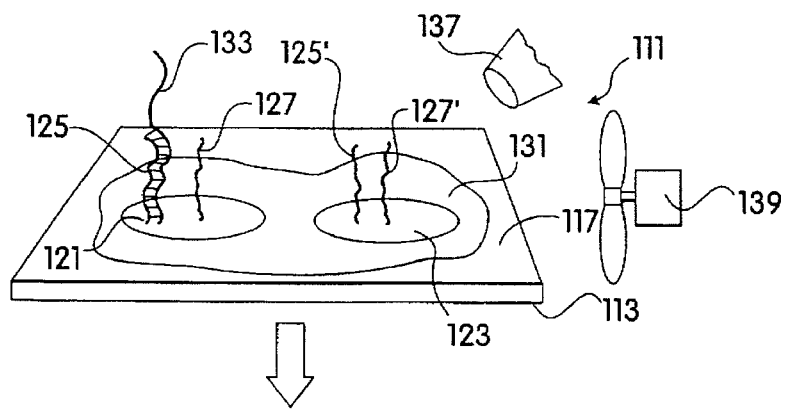
Figure 2D:
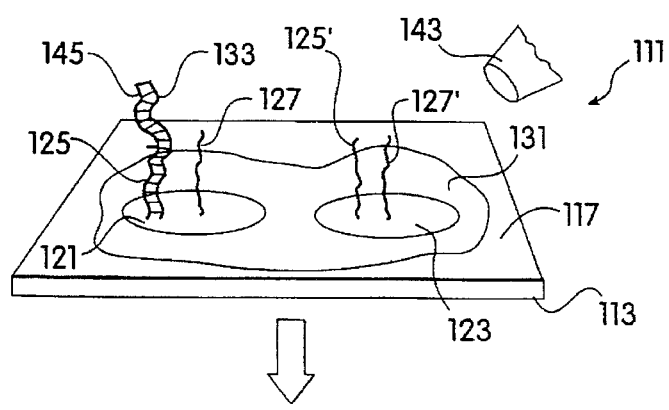

Turning now to FIG. 2C, a third work station is depicted for imposing hybridization conditions on the immersion product. Upon imposition of hybridization conditions, a hybridization product is formed in area 121 comprising a first nucleic acid 133 and a second nucleic acid 125. Hybridization conditions may comprise altering the ionic strength or pH of solutions, or lowering temperature in order to effect the hybridization of the first and second nucleic acids. Means for imposing hybridization conditions are depicted by hybridization dispensing orifice 137 and cooling fan 139.

Turning now to FIG. 1D, a fourth work station is depicted for imposing amplification conditions on the hybridization product, if present, to form a first amplification product. The first amplification product 145 comprises a nucleic acid extending from the second nucleic acid 125 corresponding to the first nucleic acid 133. Amplification conditions may comprise the addition of polymerases and transcriptases, nucleotides, buffers and the like necessary to effect an amplification reaction. Reagents to form a first amplification product 145 are dispensed through a dispensing orifice 143.

Figure 2E:
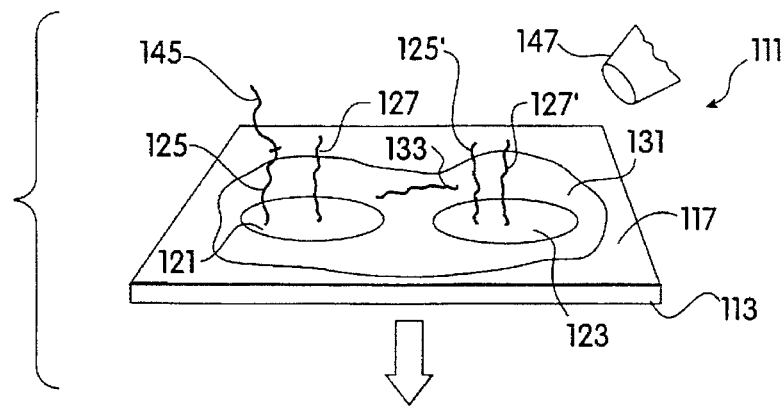

FIG. 2E depicts a fifth work station, which work station may perform one or more functions. The nucleotides incorporated into the amplification product can be labeled in order to effect detection. Thus, the fifth work station may comprise detection means [not shown] to monitor the support 113 for the presence of the amplification product. However, for most detection formats, it is useful to provide additional amplification products to increase signal. Thus, as depicted, the fifth work station imposes denaturation conditions on the amplification product 145 to allow first nucleic acid strand 133 to disassociate from second nucleic acid 125 and first amplification product 145. Denaturation reagents are dispersed on support 113 through orifice 147.

Figure 2F:
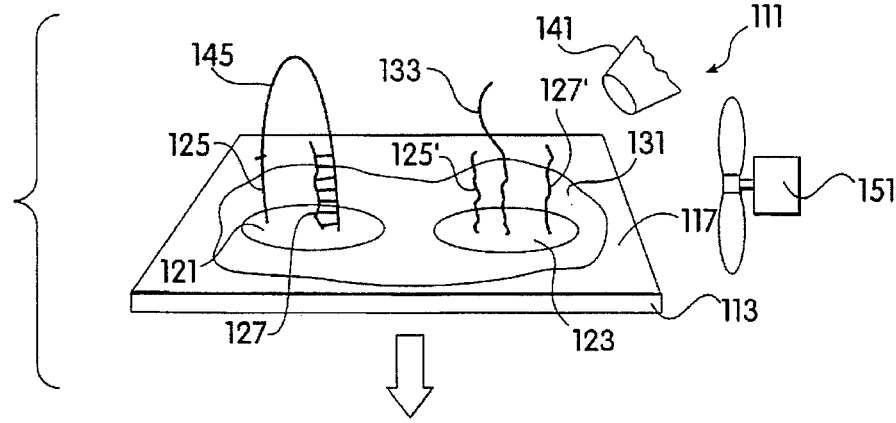

Additional signals can be obtained by again forming additional hybridization products. Turning now to FIG. 2F, a sixth work station for forming a second hybridization product is illustrated. In the event that the sample has not been removed, the first nucleic acid 133 may still remain to hybridize with nucleic acid 125' of area 123 to effect a further first hybridization product. With respect to the area 121, a second hybridization product is formed between the first amplification product 145 and third nucleic acid 127. Means for imposing hybridization conditions have been described previously. As depicted, hybridization dispensing orifice 149 and cooling fan 151 impose hybridization conditions by adding appropriate buffers, solutions, and salts, and controlling temperature.

Figure 2G:
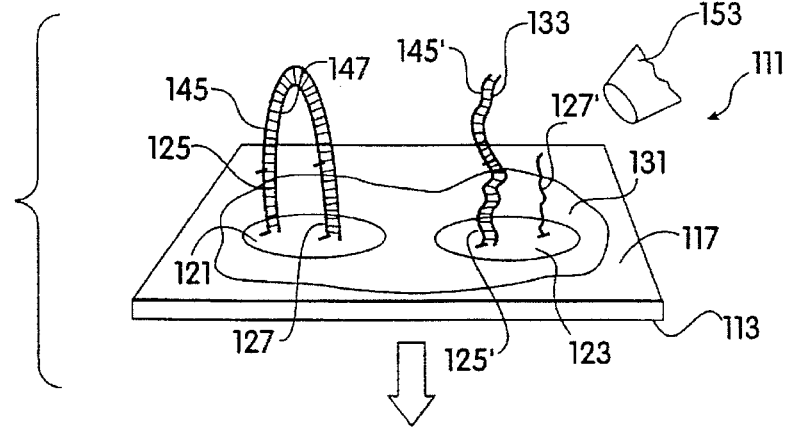

FIG. 2G depicts a seventh work station for forming a second amplification product 147 in area 121 and a further first amplification product 145' in area 123. Upon imposition of amplification conditions, a second amplification product 147 is formed in the first region 121. The second amplification product 147 comprises a nucleic acid which is complementary to the first amplification product 145. The second amplification product 147 extends from the third nucleic acid 127. A further first amplification product 145' is formed in the second area 123 extending from second nucleic acid 125'. Amplification reagents are applied to support 13 by dispensing orifice 153.

Figure 2H:
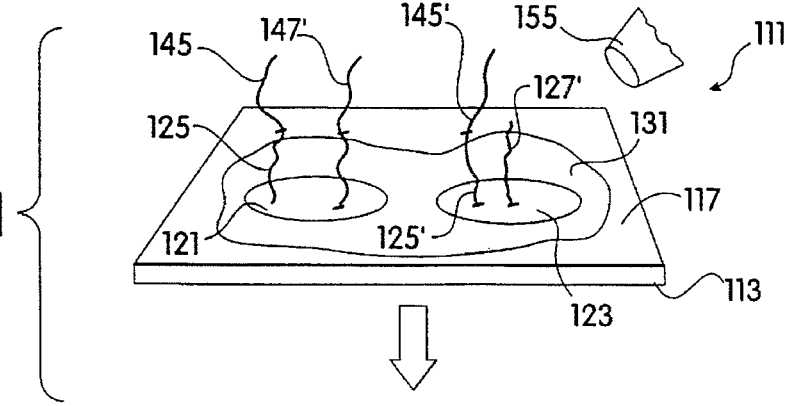

Moving now to FIG. 2H, an eighth work station is depicted for imposing denaturation conditions. After denaturation, a first and second amplification product 145 and 147 extend from the second and third nucleic acid 125 and 127 of area 121, and a first amplification product 145' extends from second nucleic acid 125' of region 123. Means for imposing denaturation conditions are depicted generally by dispensing orifice 155 and by heating elements [not shown].

Figure 2I:
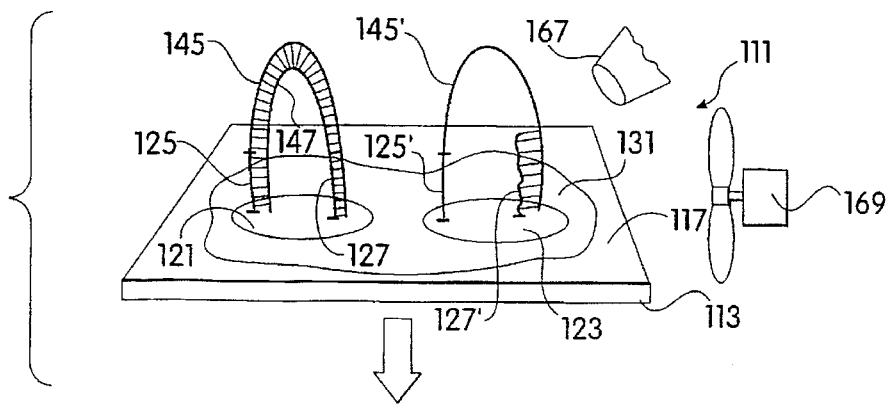

Turning now to FIG. 2I, a ninth work station is depicted for imposing hybridization conditions on the support 113. Upon imposition of hybridization conditions, the first and second amplification products 145 and 147 of area 121 hybridize; and, the first amplification product 145' of region 123 hybridizes to the third nucleic acid 127'. Means for imposing hybridization conditions comprise hybridization reagents applied through dispensing orifice 167, such as suitable buffers, salts and the like, and thermal controls represented by cooling fan 169.

Figure 2J:
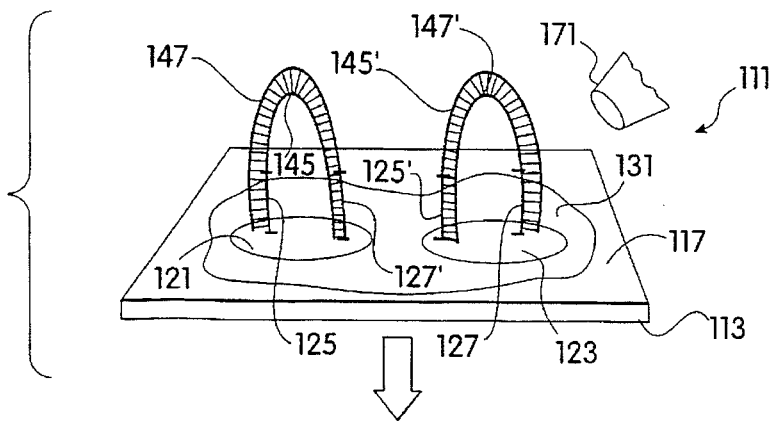

Turning now to FIG. 2J, a tenth work station is depicted for imposing amplification conditions upon the support 113. Upon imposition of amplification conditions, a second amplification product 147' is formed comprising a nucleic acid extending from third nucleic acid 127' which is complementary to the first amplification product extending from second nucleic acid 125'. Means for imposing amplification conditions comprise amplification reagents applied through dispensing orifice 174. Amplification reagents comprise buffers, salts, enzymes, nucleotides and the like.

Figure 2K:
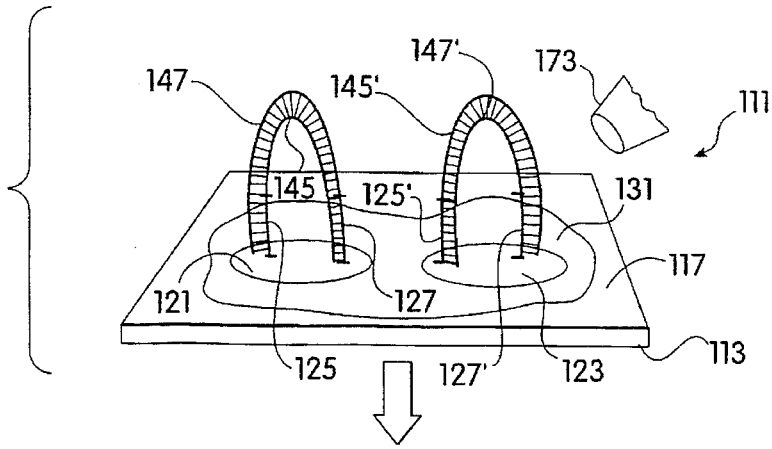

Turning now to FIG. 2K, an eleventh work station is depicted for washing the support 113. Stringent washes can be applied to remove unincorporated nucleotides and extraneous matter which may interfere with signal. As illustrated, a wash dispensing orifice 173 applies wash reagents and solutions to the support 113.

Figure 2L:
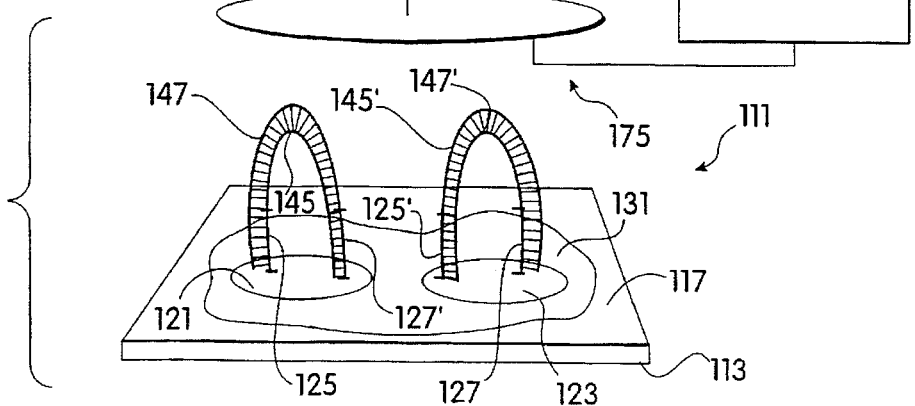

A twelfth work station, depicted in FIG. 2L, represents a detection step, in the event the method is used for diagnostic or detection purposes rather than for the synthesis of nucleic acid. Detection means 175 detects labelled nucleotides, if such nucleotides are used to form amplification products 145, 145', 147 and 147'. Detection means may comprise photosensors to detect chemiluminescent, luminescent and fluorescent or radioactive labels. Additional reagents to develop the signal are applied to the support 113.

In the event that the first and second amplification products are made with labeled nucleotides, upon imposition of detection conditions, such as the addition of cofactors or light of a wavelength of which the label is sensitive to, a signal can be developed indicating the presence of the first nucleic acid.

In the alternative, hybridization conditions can be applied to the support in the presence of intercalating agents to develop a signal in the presence of the first and second amplification products.

In addition, a fourth labeled oligonucleotide [not shown] complementary to the first or second amplification product can be used as a probe for detecting the presence of the target first oligonucleotide. A fourth nucleic acid is useful to detect only correct amplification products.

As illustrated, area 121 and 123 have identical second and third nucleic acids 125 and 127 or 125' and 127'. However, support 113 preferably has a plurality of areas which are directed to a plurality of targets. Preferably, at least one area comprises a second and third nucleic acid which have nonsense sequences. This area is intended to not produce a signal as a negative control. The presence of a signal from such second and third nucleic acids defining nonsense sequences indicates a system error.

Preferably, at least one area has a second and third nucleic acid which have sequences which correspond to a first nucleic acid, the presence of which is confirmed as being universally present or which is added to the sample. This area is intended to produce a signal in each instance as a positive control. The absence of a signal indicates a system error.

Figure 3:
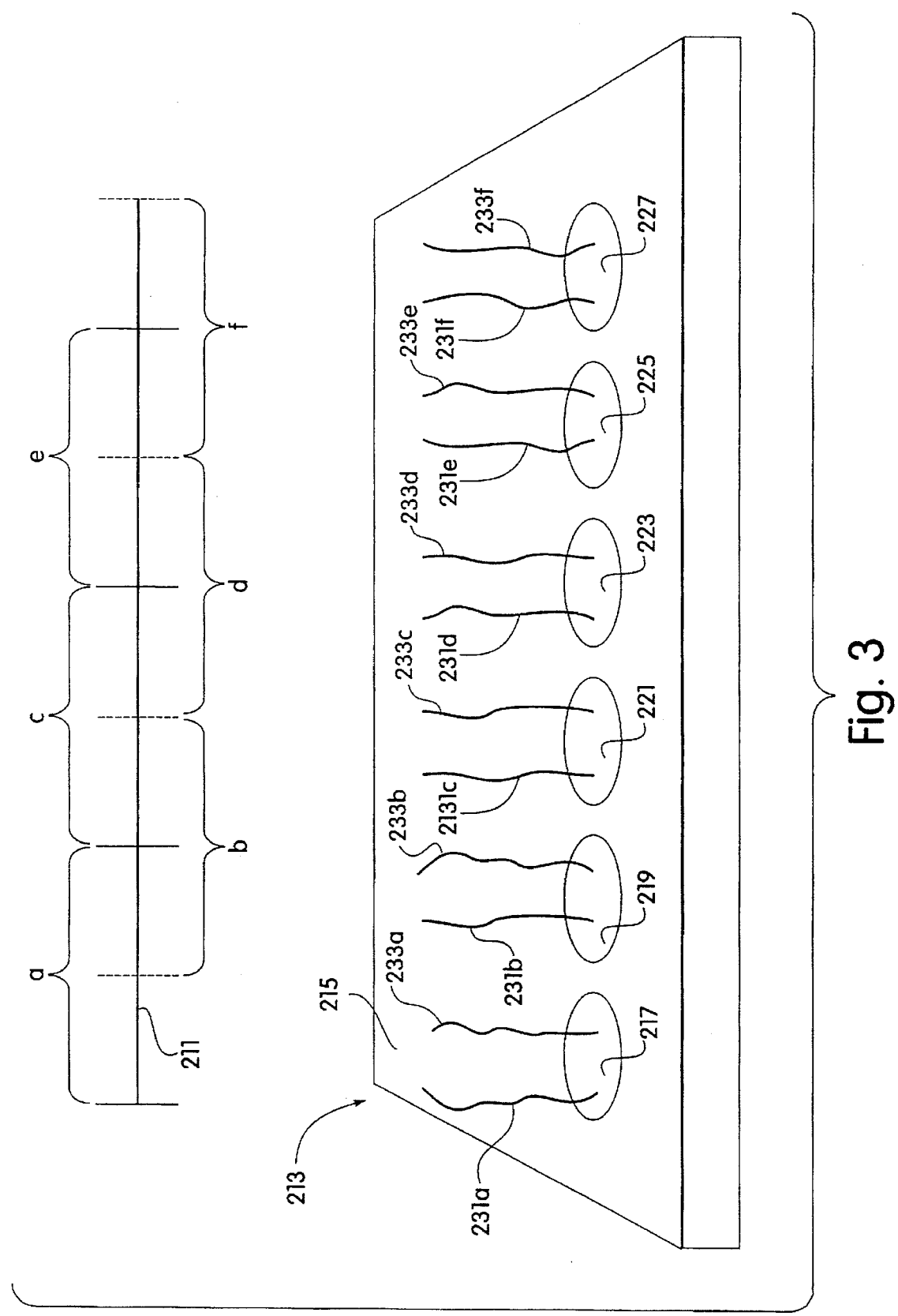
FIG. 3 depicts a article of manufacture, in the form of a support, for mapping regions of a first nucleic acid in accordance with the present invention.

Turning now to FIG. 3, a first nucleic acid generally designated by the numeral 211, is depicted. The first nucleic acid 211 has areas a through f located along its length. The device 213, for mapping regions of a first nucleic acid, has a flat planar surface 215. The surface 215 has areas 217, 219, 221, 223, 225 and 227.

Each area 217 through 227 has a second nucleic acid 231a–f respectively and a third nucleic acid 233a–f respectively. The second and third nucleic acids 231a–f and 233a–f of each area correspond to an area a–f of nucleic acid 211. Thus, the presence of a particular area on support 215 will depend on the extent in which an area a–f of nucleic acid 211 presents itself. For example, a nucleic acid 211 comprising segments b, c and d, will be detected on areas 219, 221 and 223.

In operation, the device 213 is processed in accordance with the method described with respect to FIG. 1a–1l. That is, a first nucleic acid 211, or preferably fragments of nucleic acid 211 are applied to one or more devices 213. The devices are monitored to detect the presence of an amplification product in areas 217, 219, 221, 223, 225 and 227. The presence of signal in one area with two different fragments suggests such fragments overlap. The presence of signal on two areas with one fragment suggests such areas are adjacent.

These and other features and advantages of the present invention will be revealed in the following examples which highlight preferred embodiments of the present invention.

EXAMPLES

Example 1

Formation of an Amplification Product

This example describes a method of making a first amplification product in the presence of a first nucleic acid having a target sequence. The first nucleic acid is a fragment of a larger nucleic acid sonicated to produce an approximate length of 1 kb.

A second nucleic acid is synthesized with a nucleotide sequence complementary to the target sequence of the first nucleic acid and the second nucleic acid is immobilized to an epoxy silane derivatized solid support by a 5' amino group. Spacer groups of hexaethylene-glycol are included during synthesis of the second nucleic acid to eliminate steric hindrance during the hybridization reaction. The spacer region is introduced into the synthesized oligomer prior to amino group addition, resulting in a calculated spacer region length of 25 angstroms.

The second nucleic acid is allowed to hybridize with the target DNA sequence of the first nucleic acid in the presence of thermo stable polymerase, enzyme buffer, p32 labeled and unlabeled dNTP to form a reaction mixture. The reaction mixture is heated to 94° C. for one minute, for denaturation, cooled to 55° C. for one minute, and warmed to 75° C. for 5 minutes to form an amplification product extending from the immobilized second nucleic acid and is complementary to the first nucleic acid.

The reaction mixture is washed from the reaction surface and the amplification product detected. Radiolabeled amplification products are detected using photographic film placed with the emulsion in contact with the solid support.

Example 2

Formation of Cooperating First and Second Amplification Products

This example describes a protocol for forming a first and second amplification product in the presence of a first nucleic acid having a target sequence. The first nucleic acid is derived from genomic DNA which is sonicated to produce fragments of approximately 1 kb in size.

An equimolar distribution of second and third nucleic acids, each complementary to a defined region of the plus and minus Δ 508 gene sequences are immobilized via 5' ends on a derivatized substrate, e.g. microscope slide, microtitre plates, or glass beads. The fragmented genomic DNA, is allowed to hybridize with the first and second nucleic acid in the presence of thermostable polymerase, enzyme buffer, biotin labeled and unlabeled dNTP to form a reaction mixture. The reaction mixture is heated to 94° C. for one minute, for denaturation, cooled to 55° C. for one minute, for annealing, and warmed to 75° C. for 1 minute, for amplification. After amplification the cycle of heating and cooling continues 30 times to form many first and second amplification products.

The cycling permits the first and second amplification products to hybridize to adjacent immobilized second and third nucleic acids. Upon imposition of amplification conditions, additional first and second amplification products are formed. The initial target sequence is also available to participate in further hybridization and extension reactions. The cycles may be repeated until all of the immobilized second and third nucleic acids have been extended and labeled with the appropriate nucleotides. The reaction is self-limiting and can be designed to form a predetermined number of amplification products.

The reaction mixture is washed from the reaction surface and the immobilized amplification product detected. To eliminate random background noise the reaction surface is washed using high stringency conditions.

Biotinylated amplification products are detected by analyzing the conversion of a chemiluminescent substrate by a strepavidin-alkaline phosphatase conjugate using x-ray film. Other forms of signal detection can include fluorescence microscopy, fiberoptic devices, confocal microscopy, scintillation detection, piezoelectric material and silicon based systems (charged coupled devices).

Example 3

Single Polymerase Extension

This example describes a protocol for performing a single hybridization step and polymerase step for the quantification of a first nucleic acid having a target sequence.

A plurality of second nucleic acids, each comprising two or more sequences running in the same direction, complementary to the target seqence, separated by a non-target sequence of a predetermined length are synthesized. The second nucleic acids are immobilized on a support. A sample containing the first nucleic acid is applied to the support to form an immersion product. The immersion product is subjected to denaturation, hybridization and amplification conditions. Under amplification conditions the amplification product is formed which is complementary to the target sequence and the non-target sequence simultaneously. Preferably, a single round of annealing and extension will occur. The reaction will be linear and the reaction signal will correspond directly with the number of target sequences.

The second nucleic acid can be synthesized with a sequence complementary to any target sequence. Preferably, the probe sequences are separated by 100, 200, 400 or 1000 base pairs and will form a labeled extended strand of the corresponding length. The amplification products can be detected by any suitable means dictated by the type of label used.

Example 4

Agglutination Assay

This example describes a method of detecting a first nucleic acid, HIV nucleic acid. Second and third nucleic acids of approximately 20 nucleotides in length complementary to an HIV gene sequence are immobilized onto a population of derivatized glass beads. One half of the glass beads contain the second nucleic acid and the other half contains the third nucleic acid. In this example, carboxylated derivatized latex particles may be substituted for the derivatized glass beads.

A test sample potentially containing viral nucleic acid is introduced into the reaction chamber vessel containing the glass beads to form a reaction mixture. The reaction mixture is subjected to one or more cycles of heating and cooling.

The viral nucleic acid binds to the second nucleic acid and a first reaction product is formed. This first reaction product extends from the second nucleic acid and is complementary to the third nucleic acid. Hybridization of the first amplification product to the third nucleic acid allows the formation of a second hybridization product and a second amplification product. The second amplification product is complementary to the first amplification product. Upon imposition of hybridization conditions, the beads will agglutinate or precipitate due to the binding of the first and second amplification products. The aggregated or agglutinated complex will be seen spectrophometrically as a decrease in optical density. The turbidity of the reaction solution is a function of assay sensitivity and target specificity.

Example 5

Quantitative Measurement of Bacteria Nucleic Acid

This example describes a protocol for the quantitative measurement of the amount or quantity of first nucleic acid of bacterial, viral or other origin.

Quantitative measurement of a first nucleic acid can be achieved by the immobilization of varying amounts of a substantially equimolar mixture second nucleic acid and a third nucleic acid in a panel-format. A dipstick device with a series of immobilized second nucleic acid and third nucleic acid, having varying concentrations is used as an assay to quantify bacterial contaminants in food, blood, tissue or other biological matter.

Second and third nucleic acids having a sequence complementary to the first nucleic acids are immobilized on an epoxy silane derivatized dipstick substrate via a 5' amino group. Dipstick substrates can be composed of glass, plastic, or metals. The isolated sections along the derivatized substrate receive an increasing concentration of second and third nucleic acid per unit of surface area.

An aliquot of the test sample is introduced into the reaction mixture containing, reaction buffer, polymerase and biotin labeled nucleic acids. The dipstick is placed in the reaction mixture to form an immersion product. Denaturation, hybridization and amplification conditions are imposed on the immersion product.

After a predetermined number of cycles the dipstick is removed from the reaction mixture and washed. The dipstick is then placed in a second reaction mixture comprising an avidin peroxidase conjugate and incubated for 5 minutes. The dipstick is removed from the second reaction mixture and washed. The dipstick is then placed in a developing mixture comprising a chromogenic substrate specific for peroxidase and allowed to react for 5 minutes. The dipstick is removed from the developing mixture, and monitored for color change. The fixed series of second nucleic acid concentrations in distinct areas along the dipstick and the amount of color change in each area becomes a function of the amount of bacterial cells in the test sample. For example, a test sample containing 100 bacteria is expected, after 20 reaction cycles, to cause a vivid color to occur in the dipstick sections containing 103 and 104 second nucleic acid molecules per $mm^2$.

Example 6

Mapping

This example features a protocol for mapping a first nucleic acid. A planar derivatized glass substrate receives sets of second nucleic acids. Each second nucleic acid has approximately 20 nucleotides. Each set of second nucleic acids is complementary to a different sequence corresponding to STS markers along a region of the first nucleic acid. Each set is positioned in a predetermined area of the glass support. Each set is comprised of approximately 100,000 5' amino linked second nucleic acid.

A yeast artificial chromosome (YAC) library containing first nucleic acid is divided into pools for screening. The contents of each YAC pool is applied to the support having the second nucleic acid probe array along with a reaction mixture of polymerase, buffer, and fluorescein labeled deoxy tri-nucleotides. The reaction proceeds for 30 of denaturation, hybridization and amplification. Upon completion of the reaction cycles the support is washed to remove unincorporated nucleotides and YACs.

The support is monitored by detecting the presence of amplification products that correspond to a particular YAC pool. Amplification products formed in the presence of a YAC pool in two arrays suggest that the YAC pool contains an adjacent sequence. An amplification product formed by two different YACs, suggest that the two different YACs have an overlapping sequence.

We claim:

1. A method of detecting the presence or absence of a first nucleic acid in a sample, said first nucleic acid comprising a sense strand and an antisense strand, said method comprising:

(a) forming an immersion product, said immersion product comprising said sample, said sample potentially containing said first nucleic acid and at least one primer set of nucleic acids, said nucleic acids comprising said set comprising at least one second nucleic acid and at least one third nucleic acid, said second nucleic acid and said third nucleic acid covalently affixed to a support and separated on said support by a distance less than the length of said first nucleic acid, said second nucleic acid capable of forming a hybridization product with said first nucleic acid, said third nucleic acid being complementary to the antisense strand of said first nucleic acid;

(b) forming a hybridization product comprising said first nucleic acid and said second nucleic acid, in the event said first nucleic acid is present, by imposing hybridization conditions on the immersion product;

(c) forming a first amplification product comprising said second nucleic acid extended by nucleotides complementary to said first nucleic acid, said first amplification product capable of forming a hybridization product with said third nucleic acid;

(d) denaturing the first amplification product from said first nucleic acid;

(e) forming a second hybridization product comprising said first amplification product and said third nucleic acid, by imposing hybridization conditions on the immersion product;

(f) forming a second amplification product comprising said third nucleic acid extended by nucleotides complementary to said first amplification product; and (g) monitoring said support for the presence of one of said amplification products, which presence is indicative of the presence of the first nucleic acid and which absence is indicative of the absence of said first nucleic acid wherein at least 20 rounds of amplification are performed.

2. The method of claim 1 wherein said primer set contains a plurality of second nucleic acids and a plurality of third nucleic acids, said first amplification product is capable of forming a hybridization product with a plurality of third nucleic acids and said second amplification product is capable of forming a hybridization product with a plurality of second nucleic acids, permitting a plurality of first and second amplification products to form upon the presence of first nucleic acids.

3. The method of claim 1 wherein said primer set is confined to a finite area of said support.

4. A method of mapping a first nucleic acid in a sample said first nucleic acid having a sense strand and an antisense strand, said method comprising:

(a) providing multiple copies of a first nucleic acid and dividing said first nucleic acid into a plurality of segments having overlapping sequences;

(b) providing a plurality of primer sets of nucleic acid, each primer set comprising at least a second nucleic acid and a third nucleic acid, said second nucleic acid and said third nucleic covalently affixed to a support and separated on said support by a distance less than a first segment of said first nucleic acid, said second nucleic acid capable of forming a hybridization product with a segment of said first nucleic acid, said third nucleic acid being complementary to the antisense strand of said segment, each primer set having second and third nucleic acid directed to a segment and separate from other primer sets of nucleic acids;

(c) forming an immersion product comprising the support having a plurality of primer sets of nucleic acid and a first nucleic acid segment;

(d) forming a hybridization product comprising said segment said second nucleic acid of each set, in the event said segment is present, by imposing hybridization conditions on the immersion product;

(e) forming a first amplification product comprising said second nucleic acid extended by nucleotide complementary to said segment of said first nucleic acid, said first amplification product capable of forming a hybridization product with said third nucleic acid;

(f) denaturing the first amplification product from said first nucleic acid segment;

(g) forming a second hybridization product comprising said first amplification product and said third nucleic acid, by imposing hybridization conditions on the immersion product;

(h) forming a second amplification product comprising said third nucleic acid extended by nucleotides complementary to said first amplification product;

(i) monitoring said support for the presence of one of said amplification product, which presence is indicative of the presence of the segment and which absence is indicative of the absence of said segment, said segments which form amplification products at identical sets indicating the presence of overlapping sequences of the segments wherein at least 20 rounds of amplification are performed.

5. The method of claim 1 wherein said support is an epoxy silane derivatized support.

6. The method of claim 1 wherein said second nucleic acid has a 5' amino group which 5' amino group is covalently bonded to hexaethylene glycol functional group covalently bonded to said support.

7. The method of claim 1 wherein said first nucleic acid has a size of about one to about ten kilobases.

8. The method of claim 1 wherein the amplification product is formed by imposing amplification conditions on said immersion product which amplification conditions comprise applying a thermostable polymerase to said hybridization product.

9. The method of claim 1 wherein the amplification product has a label for detection.

10. The method of claim 9 wherein the nucleotides are radiolabeled.

11. The method of claim 9 wherein the nucleotides are labeled with one or more of the group selected from chemiluminescence, radioactive, luminescent, and fluorescent agents.

12. The method of claim 1 wherein said first and second amplification products are made simultaneously.

13. The method of claim 1 wherein the amount of amplification product formed is monitored to indicate the amount of target present.

* * * * *